United States Patent
Kawakita et al.

(10) Patent No.: US 6,494,104 B2
(45) Date of Patent: Dec. 17, 2002

(54) BEND TEST FOR A WIRE HARNESS AND DEVICE FOR SUCH A TEST

(75) Inventors: Yuki Kawakita, Yokkaichi (JP); Hitoshi Kawabe, Yokkaichi (JP); Takuya Inoue, Yokkaichi (JP)

(73) Assignee: Sumitomo Wiring Systems, Ltd., Yokkaichi (JP)

( * ) Notice: Subject to any disclaimer, the term of this patent is extended or adjusted under 35 U.S.C. 154(b) by 0 days.

(21) Appl. No.: 09/812,590

(22) Filed: Mar. 21, 2001

(65) Prior Publication Data

US 2001/0029788 A1 Oct. 18, 2001

(30) Foreign Application Priority Data

Mar. 22, 2000 (JP) ........................................ 2000-079717

(51) Int. Cl.$^7$ ................................................. G01N 3/32
(52) U.S. Cl. ........................................... 73/812; 73/810
(58) Field of Search ......................... 73/774, 787, 808, 73/809, 810, 812, 814, 849, 851, 856, 860

(56) References Cited

U.S. PATENT DOCUMENTS 3,871,217 A * 3/1975 Miley ........................... 73/581
4,676,110 A * 6/1987 Hodo et al. .................... 73/809
4,869,111 A * 9/1989 Ohya et al. .................... 73/811
4,979,396 A * 12/1990 Carder et al. .................. 73/812
5,677,494 A * 10/1997 Keener et al. .................. 73/760
5,945,594 A * 8/1999 Kendig et al. ................. 204/404

FOREIGN PATENT DOCUMENTS

| DE | 873450 | 4/1953 |
| EP | 1117105 | 7/2001 |
| FR | 2711241 | 4/1995 |
| JP | 8-166333 | 6/1996 |
| WO | 01/08172 | 2/2001 |

* cited by examiner

Primary Examiner—Max Noori
(74) Attorney, Agent, or Firm—Greenblum & Bernstein, P.L.C.

(57) ABSTRACT

The invention provides a method of simulating and estimating the minimum lifetime under repeated bending for a wire harness containing a plurality of electrical cables, by applying a compact and lightly equipped device. To this end, representative electrical cables, contained in the wire harness, are subjected to flexing and stretching until they fail under repeated bending, so that the number of bending cycles is obtained for each representative electrical cable. The minimum lifetime for the wire harness can then be estimated on the basis of the shortest cable lifetime that can be found among all the representative electrical cables tested.

20 Claims, 5 Drawing Sheets

BEND TEST FOR A WIRE HARNESS AND DEVICE FOR SUCH A TEST

BACKGROUND OF THE INVENTION

1. Field of the Invention

The present invention generally pertains to a method of evaluating the bending capacity of a wire harness (WH) in order to estimate its lifetime under repeated bending. According to the present invention, the lifetime of a wire harness can be simulated or evaluated by performing bend tests with the individual electrical cables constituting the wire harness. The invention also relates to a device adapted to perform such a bend test with the individual electrical cable.

2. Description of Background Information

A wire harness is constituted by a bundle of electrical cables, with typical applications in automobiles. In the latter case, some wire harnesses are employed in opening and closing members, for instance door parts, or in sliding members such as sliding seats, in which case they receive repeated bending forces. In these wire harnesses, the constituent electrical cables are subjected to repeated bending and straining, and are thus prone to frequent breaking.

Figure 1:
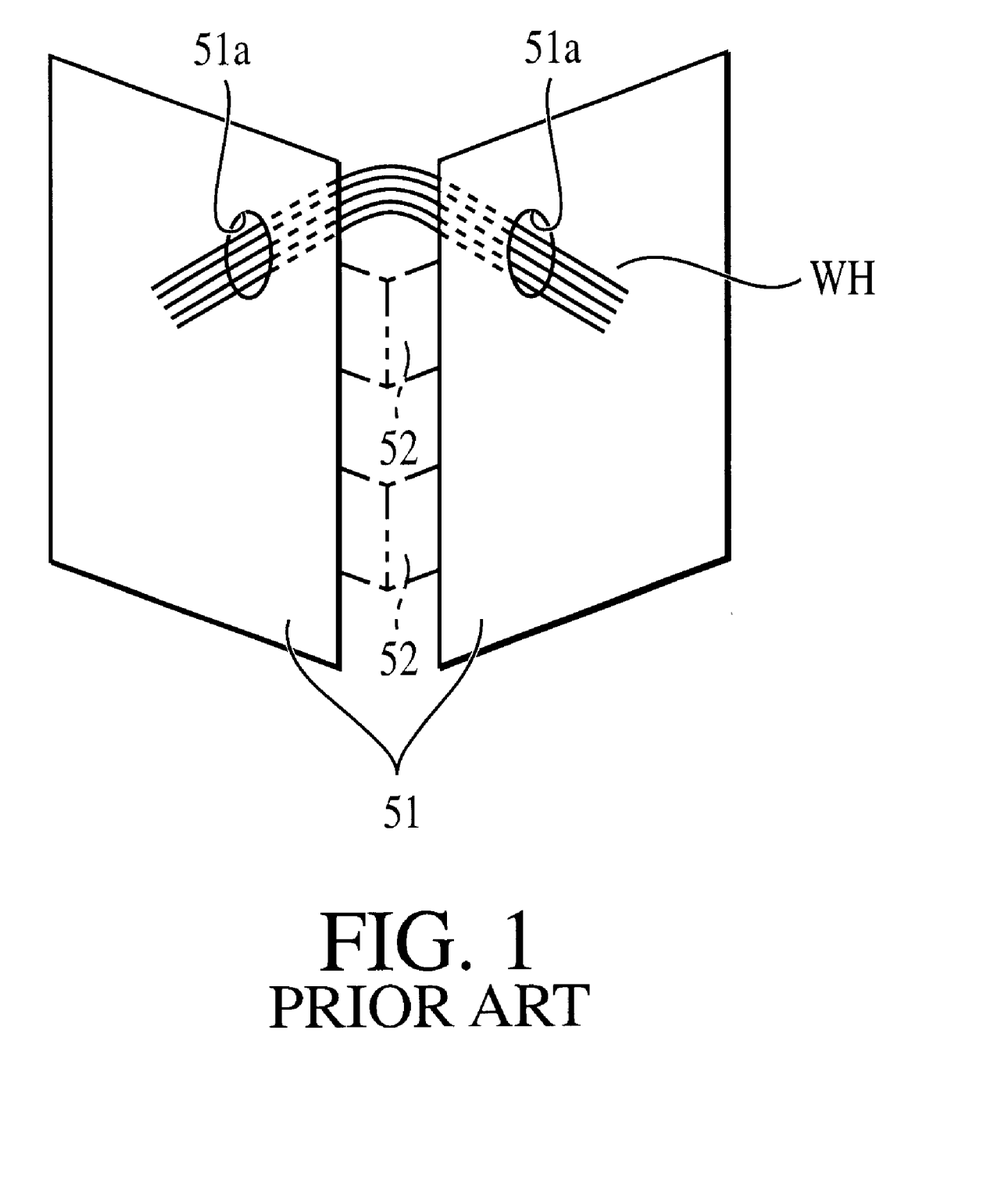
FIG. 1 is a schematic perspective view of the essential part of a known bend-test device.

In order to test the lifetime of a wire harness under repeated bending, a bend-test device such as shown in FIG. 1 is used in the prior art.

The device of FIG. 1 includes a pair of plate members 51 linked by a hinge 52 in a freely openable and closable manner. Both plate members 51 include a hole 51a, through which a wire harness can be passed. The respective end portions of the wire harness WH are passed through a corresponding hole 51a, and the wire harness WH is fixed to the plate members 51 by a fixing means (not shown in the figure). When the plate members 51 are repeatedly opened and closed by e.g. a hydraulic cylinder, the entire wire harness WH is repeatedly bent. The bend test is repeated until each electrical cable forming the wire harness is broken.

However, when a wire harness WH is tested as a bundle of electrical cables, a large-scale bend-test device must be used, whose mechanical movements are usually very slow.

At present, when using a device such as shown in FIG. 1, one bending cycle of a wire harness WH requires about 3 seconds, which is very slow in the context of the present invention.

A main object of the present invention is therefore to provide a bend-test method for evaluating the lifetime of a wire harness under repeated bending, which method can be performed by using a compact and lightly equipped testing device. This object is attained by conceiving a device for bend-testing the individual electrical cables forming a wire harness, and evaluating the wire harness lifetime from the results obtained for each electrical cable.

SUMMARY OF THE INVENTION

To this end, there is provided a method of simulating and estimating the minimum lifetime under repeated bending of a wire harness containing a plurality of electrical cables having a respective axis. The method includes selecting at least one electrical cable among a plurality of electrical cables of the wire harness, bend-testing the selected electrical cables individually until it fails, so that a limit number of bending cycles for each selected electrical cable can be obtained separately, and estimating a minimum lifetime under repeated bending for the wire harness on the basis of results obtained for each selected electrical cable.

Preferably, the selecting includes selecting one representative cable among the electrical cables belonging to the same cable category.

Preferably yet, the minimum-lifetime estimating includes choosing the shortest lifetime obtained for the bend-tested electrical cables.

Typically, the bend-testing includes providing two cable holding devices at a predetermined distance apart along the axis of the electrical cable, thereby defining a median point located substantially halfway along the predetermined distance, for each selected electrical cable, holding the selected electrical cable by the two cable holding devices, loading a weight at the median point in a direction perpendicular to the axis of the electrical cable, repeatedly bringing the two holding devices closer to, then farther from, each other, so that the selected electrical cable is reciprocatingly flexed and stretched while the weight is loaded, and repeating the above for each selected electrical cable.

Suitably, the weight-loading includes loading the weight, such as to bias the median point by about one percent, with respect to the length of the predetermined distance.

Further, the weight-loading may include providing the electrical cable with a coating, and providing in the coating a notched portion configured to retain the weight.

The invention also relates to a device for estimating the minimum lifetime under repeated bending for a wire harness containing a plurality of electrical cables having a respective axis. The inventive device is configured to bend-test at least one of the electrical cables individually, until it fails, so that a limit number of bending cycles for each of the electrical cables can be obtained separately.

The device preferably includes two cable holding devices, located at a predetermined distance apart along the axis of the electrical cable and configured to hold the latter, so as to define a median point located substantially halfway along the predetermined distance.

The device further includes a driving mechanism, such that the two cable holding devices can be repeatedly brought closer to, then farther from, each other in a reciprocating manner.

Preferably, the cable holding devices include a corresponding holding member including an elastic material portion configured to hold the electrical cable, such that the elastic material portion prevents the electrical cable from compressive strain.

The device may further include a device for biasing the median point by about one percent, with respect to the length of the predetermined distance.

BRIEF DESCRIPTION OF THE DRAWINGS

The above and the other objects, features and advantages of the present invention will be made apparent from the following description of the preferred embodiments, given as non-limiting examples, with reference to the accompanying drawings, in which:

FIGS. 5A and 5B schematically illustrate a case of the first variant of FIG. 3, in which

DETAILED DESCRIPTION OF THE PREFERRED EMBODIMENTS

When evaluating the lifetime of a wire harness according to a first embodiment of the invention, the wire harness is first disassembled into a plurality of constituent electrical cables. Each constituent electrical cable is then subjected to a bend test. The lifetime of the integral wire harness is then estimated or evaluated on the basis of the test results for each constituent electrical cables.

The bent test for each electrical cable is performed as explained hereafter.

Figure 2:
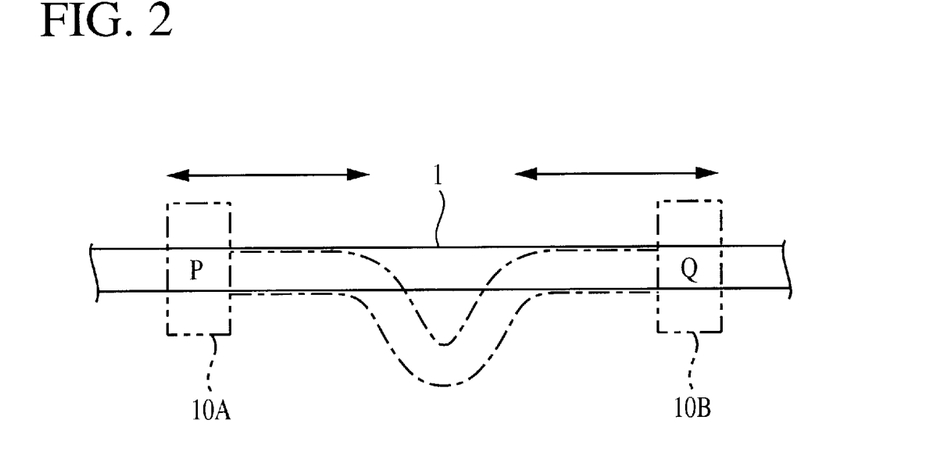
FIG. 2 illustrates the principle of a flexing and stretching mechanism applied to an electrical cable, according to a first embodiment of the invention.

As shown in FIG. 2, an electrical cable 1 forming part of a wire harness WH is held by a pair of fixing devices 10A and 10B, which are located respectively at positions P and Q, separated by a given distance. The fixing devices 10A and 10B are then moved closer to each other, or returned to the initial positions along the longitudinal axis of the electrical cable 1. Stress is thus created at a median point of electrical cable, located substantially halfway between positions P and Q, so that the electrical cable 1 is flexed or stretched, with the median point serving as flex center. FIG. 2 illustrates a stretched state of the cable expressed by continuous lines, and a flexed state expressed by dotted lines. Flexing and stretching movements are repeated until the wire core of the electrical cable 1 breaks or fails. In order to detect the failing moment in the wire core, a conductivity tester including anode and cathode terminals, for instance, can be installed. When such a tester is used, the anode terminal is electrically connected to one end of the wire core, while the cathode terminal is likewise connected to the other end thereof. When the two terminals become electrically disconnected, the electrical cable is considered to be actually severed. The number of bending movements, repeated until such a moment, indicates the lifetime of an electrical cable 1 under repeated bending.

Such a bend test is performed individually for all the electrical cables 1 constituting a wire harness WH in question. The results obtained for all the electrical cables are then compared, and the shortest lifetime among them is recorded. This shortest lifetime gives an estimation for the lifetime of the wire harness WH under repeated bending.

When the wire harness WH contains several electrical cables 1 belonging to a same category, they can be reasonably regarded as having the same lifetime under repeated bending. It will then suffice to test only one such electrical cable 1 as representative for the same category of electrical cables.

When such an estimation method is adopted for evaluating the lifetime of a wire harness WH, it suffices to provide a compact and lightly-equipped bend-test machine for testing individual electrical cables, instead of testing a unitary wire harness WH.

In the course of the above test, an electrical cable 1 receives alternating buckling and stretching forces along its longitudinal axis. As a consequence, the electrical cable is flexed and redressed in a reciprocating way.

However, when the buckling and stretching forces are imparted merely along the longitudinal axis, the median point of the electrical cable 1 may drift in a random direction, e.g. upwardly or downwardly, or leftward or rightward, perpendicular to the longitudinal axis. If the median point is flexed towards different directions each time it is buckled, the bend test cannot indicate a precise lifetime span under repeated bending.

Accordingly, the median point of the electrical cable 1, located halfway between positions P and Q, is preferably subjected to a lateral force W (note FIG. 5B), such that the flexing movements are oriented to one given direction perpendicular to the longitudinal axis of the cable 1, while buckling or stretching forces are imparted.

Figure 3:
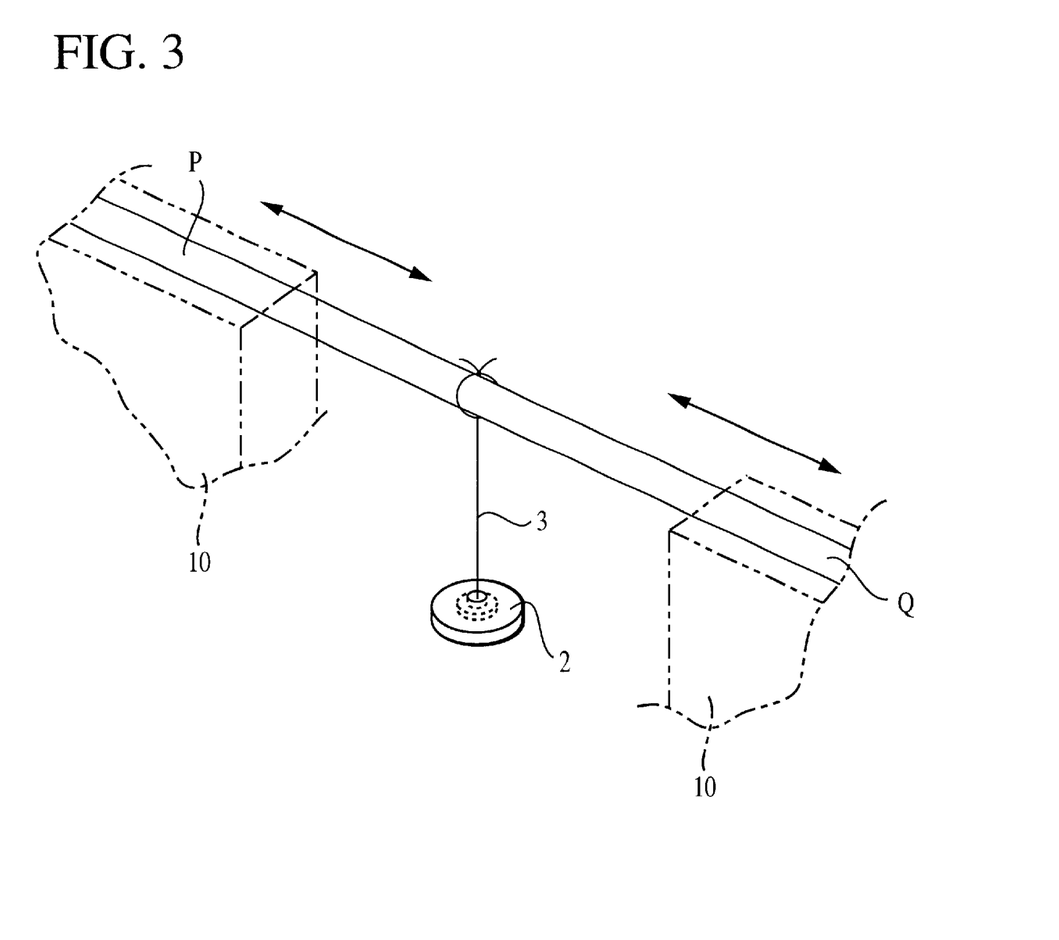
FIG. 3 is a perspective view of a first variant of the first embodiment of FIG. 2, in which a weight is loaded.

To this end, a weight 2 may be hung at the median point through a thread or cord 3 as shown in FIG. 3. The weight 2 may have any shape including a disk and a ball.

In this condition, the median point is always stressed downwardly, so that, when the electrical cable 1 is buckled, the median point is biased also downwardly.

In this manner, the electrical cable 1 may be flexed always in a predetermined direction, which is perpendicular to the longitudinal axis of the cable 1. A precise bend test can thus be carried out in an easy manner.

Figure 4:
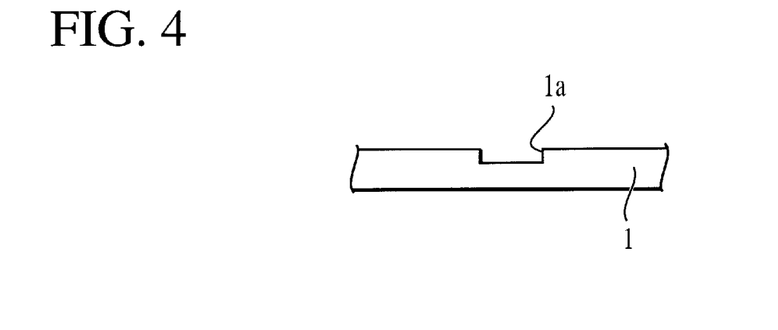
FIG. 4 is a side view of an electrical cable used in a second variant of the first embodiment of FIG. 2, in which a portion of the electrical cable is notched.

To avoid the weight 2 being biased along the longitudinal axis of the cable 1 while testing, coatings of the cable 1 may be provided with a recess 1a (FIG. 4), by which the thread or cord 3 is hooked or hung.

Such a lateral force W must be able to flex the electrical cable 1 towards a predetermined direction, but should not affect test results. To satisfy such prerequisites, the lateral force W is preferably strong enough to bias the median point by one percent in the lateral (perpendicular) direction, relative to the length (taken as 100%) of the distance between positions P and Q.

Figure 5A:
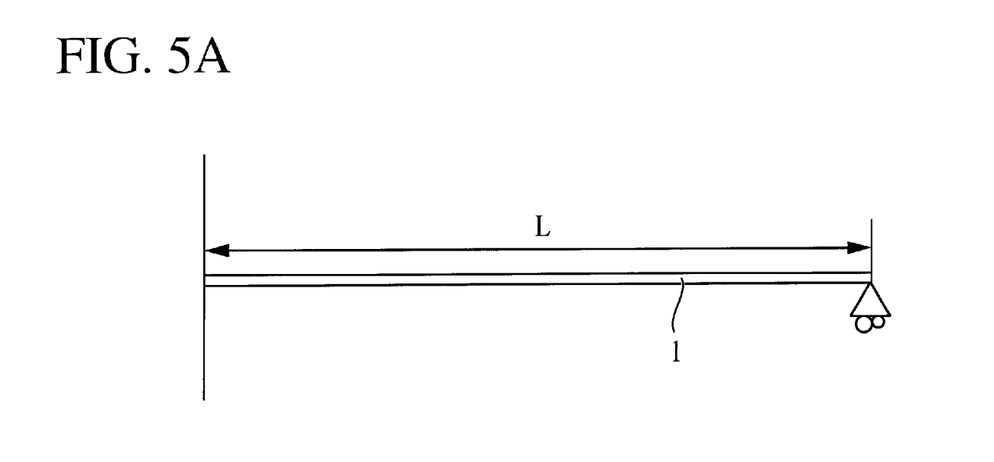
FIG. 5A shows an electrical cable when its two ends are fixedly held.
Figure 5B:
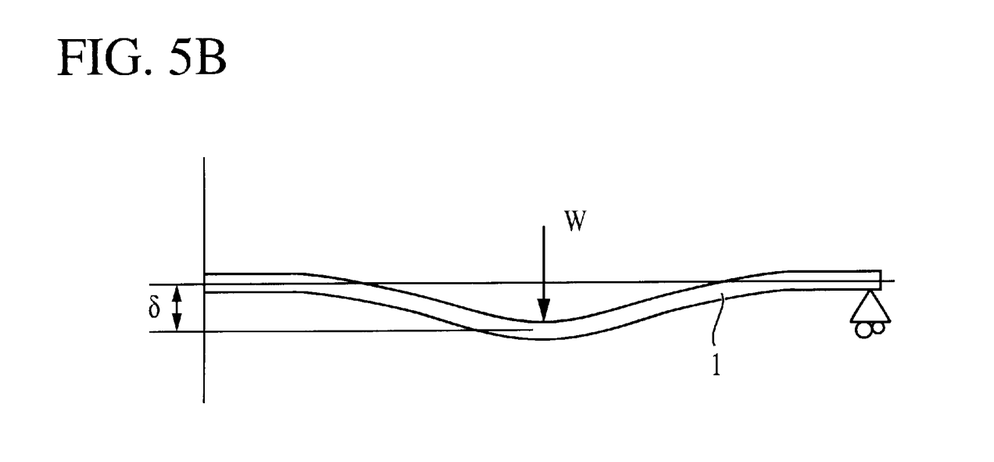
FIG. 5B shows when it is loaded with a weight.

FIG. 5A shows an electrical cable 1 having a length L, with its two ends fixedly held. When a lateral force W is exerted on the median point (FIG. 5B), a displacement δ of the electrical cable 1 can be calculated on the basis of a formula provided for a rod held on two supporting points, as follows:

$$\delta = WL^3/(48EI) \tag{I}$$

where L is the effective length of an electrical cable 1 (distance between P and Q in the cases of FIGS. 2 and 3), E is the Young's modulus, I is a two-dimensional moment of a section represented by the formula I=rd$^4$/64, and d signifies the diameter of an electrical cable 1.

A lateral displacement of 1% relative to the length of an electrical cable 1 can be represented by the formula:

$$\delta = L/100 \tag{II}$$

in which δ and L are as defined by formula (I).

Preferably, a lateral force W is chosen such as to satisfy the above formula (I) and (II). When compared with the examples of the invention, such a lateral force W is the sum of a first lateral force w1 originating from the weight 2 and a second lateral force w2 originating from the thread or cord 3.

In order to implement the bend-test method according to the first embodiment, there is provided a bend-test device for the electrical cables, which are the constituents of a wire harness, according to a second embodiment of the invention.

Figure 6:
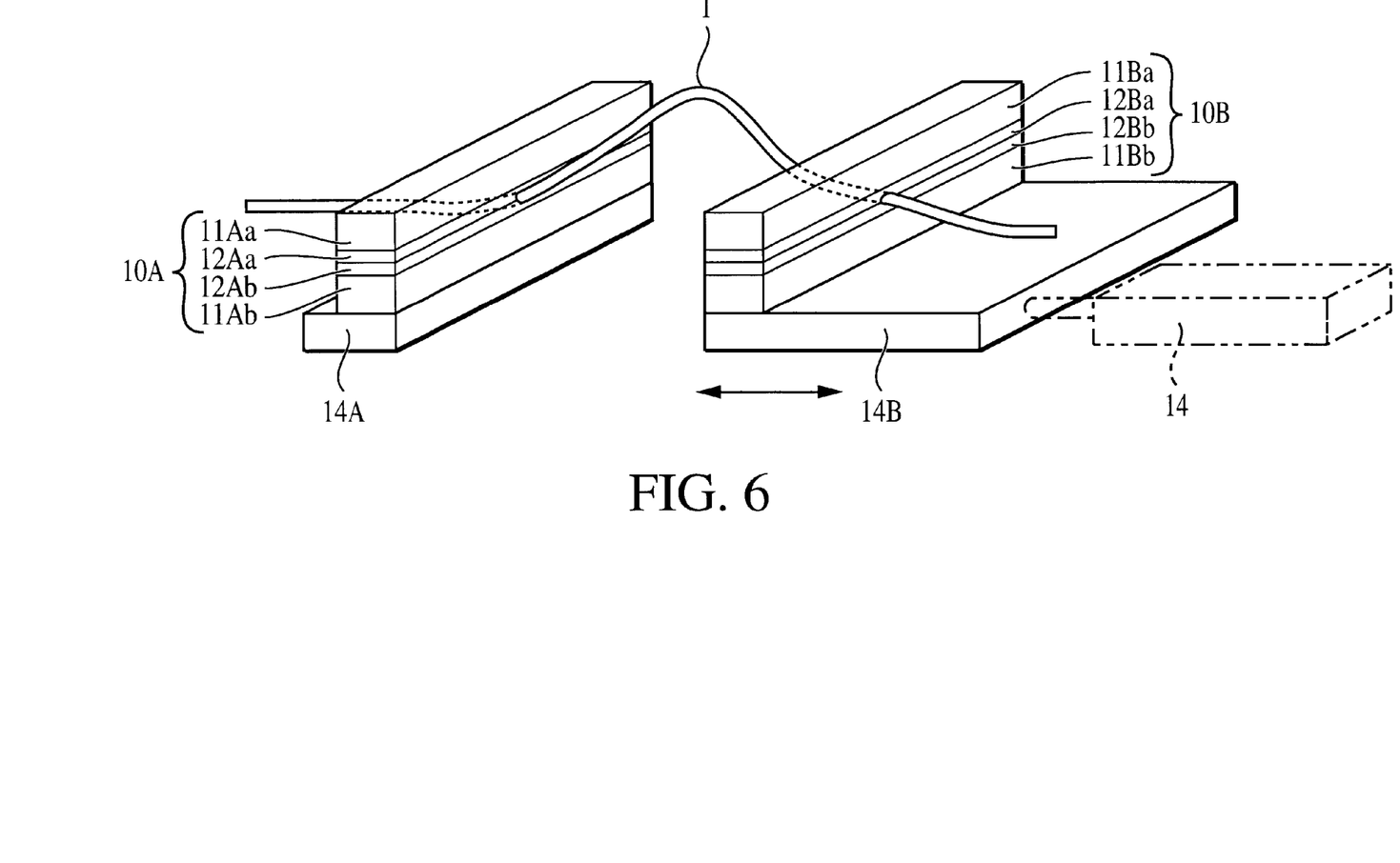
FIG. 6 is a perspective view of a bend-test device according to a second embodiment of the invention.

FIG. 6 shows such a device, which includes a pair of cable holding devices 10A and 10B and a driving mechanism 14 which brings one of the cable holding devices (e.g. 10B) closer to, or farther from, the other cable holding device (e.g. 10A).

The cable holding device 10A includes a pair of holding members 11A*a* and 11A*b* having a generally rectangular form. These holding members 11A*a* and 11A*b* are superposed on each other, so as to hold an electrical cable 1 therebetween, and then clamped by e.g. a screw in a direction perpendicular to the cable's axis (vertical direction in FIG. 6).

However, when the electrical cable 1 is held in this manner, it may be deformed by the clamping stress. To avoid this, a pair of elastic material portions or elastic members 12A*a* and 12A*b* may be provided between the above-mentioned holding members 11A*a* and 11A*b* (note FIGS. 8A and 8B), so that the electrical cable 1 is held only through these elastic material portions 12A*a* and 12A*b*. The elastic material portions may be formed of any suitable material, e.g. a rubber material.

By using the elastic material portions 12A*a* and 12A*b*, the following advantageous effects can be obtained.

Figure 7A:
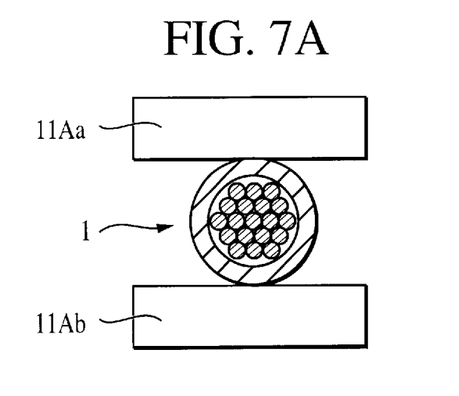
FIGS. 7A and 7B are respectively a partial cross-sectional view of an electrical cable, when it is set between a pair of holding members lacking elastic material portions (FIG. 7A), and when it is compressed (FIG. 7B)
Figure 7B:
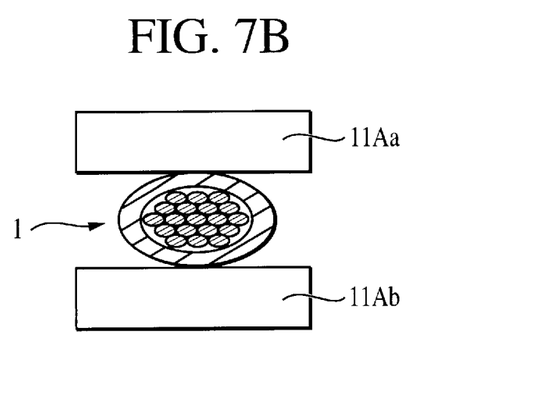

FIGS. 7A and 7B show how the holding members 11A*a* and 11A*b* seize the electrical cable 1, when they are directly applied. As can be immediately understood, the electrical cable 1 may be compressed by a clamping force in the vertical direction in FIG. 6. If the cable holding device 10B is brought closer to the other cable holding device 10A in this condition, the electrical cable 1 may tend to be bent in the zone where it is compressed, i.e. where the holding members 11A*a* and 11A*b* are located. As a consequence, the wire core contained in the electrical cable 1 may be broken in that zone, in which case a precise bend test cannot be carried out.

Figure 8A:
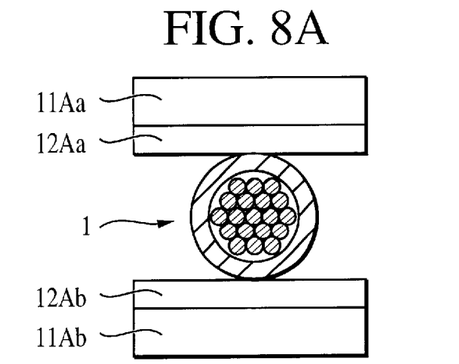
FIGS. 8A and 8B are respectively a partial cross-sectional view of an electrical cable, when it is set between a pair of holding members including elastic material portions (FIG. 8A), and when it is compressed (FIG. 8B).
Figure 8B:
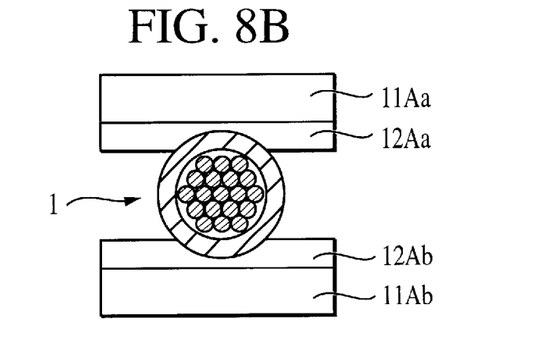

When the elastic material portions 12A*a* and 12A*b* are mounted in a zone in contact with the electrical cable 1, which zone is interposed between the holding members 11A*a* and 11A*b*, the electrical cable 1 is held by the elastic deformation of these elastic material portions 12A*a* and 12A*b*, so that the electrical cable 1 can be efficiently prevented from the deformation due to compression.

As a result, the electrical cable 1 is prevented from flexing in the periphery of the first cable holding device 10A. The median point of the electrical cable 1 thus becomes the main flexing point, and precise bend tests can be performed in a reliable way.

The second cable holding device 10B is constructed as in the case of the first cable holding device 10A: holding members 11B*a* and 11B*b* are superposed, and the zone of holding members 11B*a* and 11B*b* where the cable 1 is in contact with the electrical cable is provided with elastic material portions or elastic members 12B*a* and 12B*b*.

The first cable holding device 10A is mounted on a immobilized base 14A fixedly installed on a working bench (FIG. 6). Conversely, the second cable holding device 10B is mounted on a movable base 14B which is installed on the working bench in a freely movable manner so that it can be brought closer to, or farther from, the immobilized base 14A. Typically, the first and second cable holding devices 10A and 10B include, respectively, rectangular-shaped holding members 11A and 11B. The first and second cable holding devices 10A and 10B are then placed in such a way that these rectangular shapes are arranged in parallel relation to each other, in a direction perpendicular to the movement axis, i.e. longitudinal axis of the electrical cable. They are then brought closer to, or farther from, each other in a freely movable manner.

Further, the movable base 14B is linked to a drive or piston mechanism 14, which may include pneumatic ram. This drive mechanism 14 gives repeated movements to the movable base 14B, by pushing it towards, and pulling it farther from, the immobilized base 14A.

In such a bend-test device, the first and second cable holding devices 10A and 10B are first arranged in the farthest position from each other. A stretched electrical cable 1 is then held by the holding members 11A*a* and 11A*b* of the first cable holding device 10A on the one hand, and the holding members 11B*a* and 11B*b* of the second cable holding device 10B, on the other. The first and second cable holding devices 10A and 10B are then subjected to closing and separating movements caused by the drive mechanism 14. When the first and second cable holding devices 10A and 10B are brought closer to each other, the electrical cable 1 is imparted with a buckling force in its longitudinal direction, and the median point of the cable 1 is flexed and deformed. When the first and second holding devices 10A and 10B are moved farther from each other, the electrical cable 1 is stretched in its longitudinal direction, and deformed back. As this movement is repeated, flexing and stretching deformation of the median point is also repeated. The approaching-and-separating movements are repeated until the electrical cable 1 breaks or fails, and the number of the movements of second cable holding device 10B up to this break or failure point is counted. The bend frequencies thus obtained are defined as the lifetime of the electrical cable 1 under repeated bending.

Further, there may be provided a conductivity-detection unit for detecting the break of the wire core of electrical cable 1, and a counting unit for counting the reciprocating movements of second cable holding device 10B, which are recorded up to the break (failure) point detected by the conductivity-detection unit. In this manner, when an electrical cable 1 is set into the bend-test device of the invention, its lifetime under repeated bending can be automatically recorded.

According to the above device, the holding members 11A*a* and 11A*b* (or 11 B*a* and 11B*b*) may include a corresponding elastic material portion 12A*a* and 12A*b* (or 12B*a* and 12B*b*), which is formed of an elastic material and seizes the electrical cable 1. When the first and second cable holding devices 10A and 10B hold the electrical cable 1, the elastic material portions 12A*a* and 12A*b* (or 12B*a* and 12B*b*) are elastically deformed, so that the electrical cable 1 itself can avoid the deformation due to compression. Consequently, the electrical cable 1 is prevented from flexing in proximity of the first and second cable holding devices 10A and 10B. As a result, the electrical cable 1 is flexed at the median point, and the bend tests can be effected correctly.

The bend-test device of the present invention handles each electrical cable 1 individually, so that it has a much simpler structure than a bend-test device such as shown in FIG. 1, which handles a unitary wire harness.

The inventive device thus has a compact structure better adapted to swift movements. For instance, the electrical cable 1 can be flexed at a rate of 5 times (cycles) per second.

By comparison, the device of FIG. 1 takes about 3 seconds for one flexing of a wire harness. Moreover, it takes 2000 to 3000 flexing cycles for a wire harness, until the last constituent electrical cable fails. Testing of a wire harness thus requires a considerable amount of time in the prior art.

Accordingly, for certain types of wire harness, their lifetime can be measured more rapidly by testing individual electrical cables 1 than testing by a unitary wire harness WH.

As already mentioned, according to the inventive method, bend tests are carried out with each electrical cable constituting a wire harness separately, until the electrical cable in question fails. The lifetime of the wire harness is then estimated on the basis of the result obtained for each electrical cable. The bend tests can therefore be conducted more easily by using a compact, lightly equipped test device.

Further, the median point of an electrical cable, located halfway between the first and second cable holding devices, is imparted with a load towards a direction perpendicular to the axis of the electrical cable. Thereafter, the holding devices are brought closer to each other, and brought farther from each other, so that the electrical cable is flexed and stretched in a reciprocating manner. In this manner, the electrical cable is flexed always in the same direction, and the bend tests give highly reliable results.

Furthermore, in the inventive bend-test device for electrical cables, there is provided a pair of cable holding devices carrying a corresponding holding member adapted to hold an electrical cable. Both cable holding devices are mounted such that they can be brought closer to each other, or farther from each other, in a freely movable manner. There is also provided a driving mechanism for reciprocating a cable holding device. Further, the holding members include, respectively, an elastic material portion for clamping the electrical cable. When the electrical cable is held, the elastic material portion is elastically strained, so that the electrical cable itself can avoid the compressive strain. Moreover, when effecting bend tests, the electrical cable is properly flexed at the median point thereof, and not at the proximity of the cable holding devices.

Although the invention has been described with reference to particular means, materials and embodiments, it is to be understood that the invention is not limited to the particulars disclosed and extends to all equivalents within the scope of the claims.

The present disclosure relates to subject matter contained in priority Japanese Application No. 2000-079717, filed on Mar. 22, 2000, which is herein expressly incorporated by reference in its entirety.

What is claimed:

1. A method of simulating and estimating a minimum lifetime under repeated bending of a wire harness containing a plurality of electrical cables having a respective axis, said method comprising:
    selecting at least one electrical cable among said plurality of electrical cables;
    bend-testing said selected electrical cable individually until it fails, so that a limit number of bending cycles for each said selected electrical cable is obtainable separately; and
    estimating said minimum lifetime under repeated bending for said wire harness on the basis of results obtained for each said selected electrical cable.

2. The method according to claim 1, wherein said selecting comprises selecting one representative cable among the electrical cables belonging to a same cable category.

3. The method according to claim 1, wherein said minimum-lifetime estimating comprises choosing the shortest lifetime obtained for said bend-tested electrical cables.

4. The method according to claim 2, wherein said minimum-lifetime estimating comprises choosing the shortest lifetime obtained for said bend-tested electrical cables.

5. The method according to claim 1, wherein said bend-testing comprises:
    providing two cable holding devices at a predetermined distance apart along said axis of the electrical cable, thereby defining a median point located substantially halfway along said predetermined distance, for each said selected electrical cable;
    holding said selected electrical cables by said two cable holding devices;
    loading a weight at said median point in a direction perpendicular to said axis of said electrical cable;
    repeatedly bringing said two holding devices closer to, then farther from, each other, so that said selected electrical cable is flexed and stretched in a reciprocating manner while said weight is loaded; and
    repeating the above for each of said selected electrical cables.

6. The method according to claim 2, wherein said bend-testing comprises:
    providing two cable holding devices at a predetermined distance apart along said axis of the electrical cable, thereby defining a median point located substantially halfway along said predetermined distance, for each said selected electrical cable;
    holding said selected electrical cables by said two cable holding devices;
    loading a weight at said median point in a direction perpendicular to said axis of said electrical cable;
    repeatedly bringing said two holding devices closer to, then farther from, each other, so that said selected electrical cable is flexed and stretched in a reciprocating manner while said weight is loaded; and
    repeating the above for each of said selected electrical cables.

7. The method according to claim 3, wherein said bend-testing comprises:
    providing two cable holding devices at a predetermined distance apart along said axis of the electrical cable, thereby defining a median point located substantially halfway along said predetermined distance, for each said selected electrical cable;
    holding said selected electrical cables by said two cable holding devices;
    loading a weight at said median point in a direction perpendicular to said axis of said electrical cable;
    repeatedly bringing said two holding devices closer to, then farther from, each other, so that said selected electrical cable is flexed and stretched in a reciprocating manner while said weight is loaded; and
    repeating the above for each of said selected electrical cables.

8. The method according to claim 4, wherein said bend-testing comprises:
    providing two cable holding devices at a predetermined distance apart along said axis of the electrical cable, thereby defining a median point located substantially halfway along said predetermined distance, for each said selected electrical cable;
    holding said selected electrical cables by said two cable holding devices;
    loading a weight at said median point in a direction perpendicular to said axis of said electrical cable;

repeatedly bringing said two holding devices closer to, then farther from, each other, so that said selected electrical cable is flexed and stretched in a reciprocating manner while said weight is loaded; and repeating the above for each of said selected electrical cables.

9. The method according to claim 5, wherein said weight-loading comprises loading the weight, so as to bias said median point by about one % (percent), with respect to the length of said predetermined distance.

10. The method according to claim 6, wherein said weight-loading comprises loading the weight, so as to bias said median point by about one % (percent), with respect to the length of said predetermined distance.

11. The method according to claim 7, wherein said weight-loading comprises loading the weight, so as to bias said median point by about one % (percent), with respect to the length of said predetermined distance.

12. The method according to claim 8, wherein said weight-loading comprises loading the weight, so as to bias said median point by about one % (percent), with respect to the length of said predetermined distance.

13. The method according to claim 5, wherein said weight-loading comprises providing said electrical cable with a coating, and providing in said coating a notched portion adapted to retain said weight.

14. The method according to claim 6, wherein said weight-loading comprises providing said electrical cable with a coating, and providing in said coating a notched portion configured to retain said weight.

15. The method according to claim 7, wherein said weight-loading comprises providing said electrical cable with a coating, and providing in said coating a notched portion configured to retain said weight.

16. The method according to claim 8, wherein said weight-loading comprises providing said electrical cable with a coating, and providing in said coating a notched portion configured to retain said weight.

17. A device for estimating the minimum lifetime under repeated bending of a wire harness containing a plurality of electrical cables having a respective axis, said device being configured to bend-test at least one of the electrical cables individually, until it fails, so that a limit number of bending cycles for each of the electrical cables is obtainable separately;

said device comprising two cable holding devices, located at a predetermined distance apart along the axis of the electrical cable and configured to hold the latter, so as to define a median point located substantially halfway along said predetermined distance;

said device comprising a driving mechanism and configured to repeatedly bring said two cable holding devices closer to, then farther from, each other in a reciprocating manner.

18. The device according to claim 17, wherein said cable holding device comprises a corresponding holding member including an elastic material portion configured to hold said electrical cable.

19. The device according to claim 17, further comprising a device for biasing said median point by about one % (percent), with respect to the length of said predetermined distance.

20. The device according to claim 19, further comprising a device for biasing said median point by about one % (percent), with respect to the length of said predetermined distance.

* * * * *

UNITED STATES PATENT AND TRADEMARK OFFICE
CERTIFICATE OF CORRECTION

PATENT NO.     : 6,494,104 B2
DATED          : December 17, 2002
INVENTOR(S)    : Y. Kawakita et al.

It is certified that error appears in the above-identified patent and that said Letters Patent is hereby corrected as shown below:

<u>Title page,</u>
Item [56], References Cited, FOREIGN PATENT DOCUMENT, include:

-- JP    7-146226    06/06/95 --.

Signed and Sealed this

Twelfth Day of August, 2003

JAMES E. ROGAN
*Director of the United States Patent and Trademark Office*